United States Patent [19]

Werner et al.

[11] 3,988,208

[45] *Oct. 26, 1976

[54] 9-SUBSTITUTED 3-AMINOCARBAZOLE COMPOUNDS AND TEST STRIP INDICATOR COMPOSITIONS

[75] Inventors: Wolfgang Werner, Mannheim-Vogelstang; Peter Vogel, Weinheim; Hugo Tiedemann, Mannheim-Wallstadt; Werner Güthlein, Mannheim-Neckarau im Sennteich, all of Germany

[73] Assignee: Boehringer Mannheim G.m.b.H., Mannheim-Waldhof, Germany

[ * ] Notice: The portion of the term of this patent subsequent to July 2, 1991, has been disclaimed.

[22] Filed: Mar. 17, 1975

[21] Appl. No.: 559,273

Related U.S. Application Data

[62] Division of Ser. No. 487,338, July 10, 1974.

[30] Foreign Application Priority Data

Aug. 1, 1973  Germany............................ 2338932

[52] U.S. Cl. .................. 195/103.5 C; 195/103.5 R
[51] Int. Cl.² .......................................... C12K 1/04
[58] Field of Search .............. 195/103.5 C, 103.5 R; 424/7; 260/315

[56] References Cited
UNITED STATES PATENTS
3,822,285  7/1974  Werner et al...................... 260/315

Primary Examiner—A. Louis Monacell
Assistant Examiner—C. A. Fan
Attorney, Agent, or Firm—Burgess, Dinklage & Sprung

[57] ABSTRACT

Novel 3-aminocarbazole compounds of the formula:

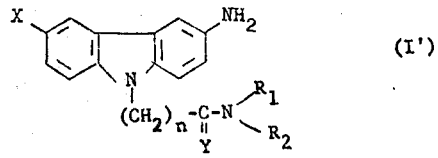

wherein
X is hydrogen or halogen,
Y is oxygen or represents two hydrogen atoms; and
$R_1$ and $R_2$, which can be the same or different, are hydrogen, lower alkyl or hydroxyalkyl or amino; and
n is 1 or 2, with the proviso that when n is 2, X, Y, $R_1$ and $R_2$ cannot all be hydrogen atoms, as well as the salts thereof with inorganic and organic acids; are outstandingly effective indicators for the determination of glucose and provide stable compositions for such glucose determination.

15 Claims, 1 Drawing Figure

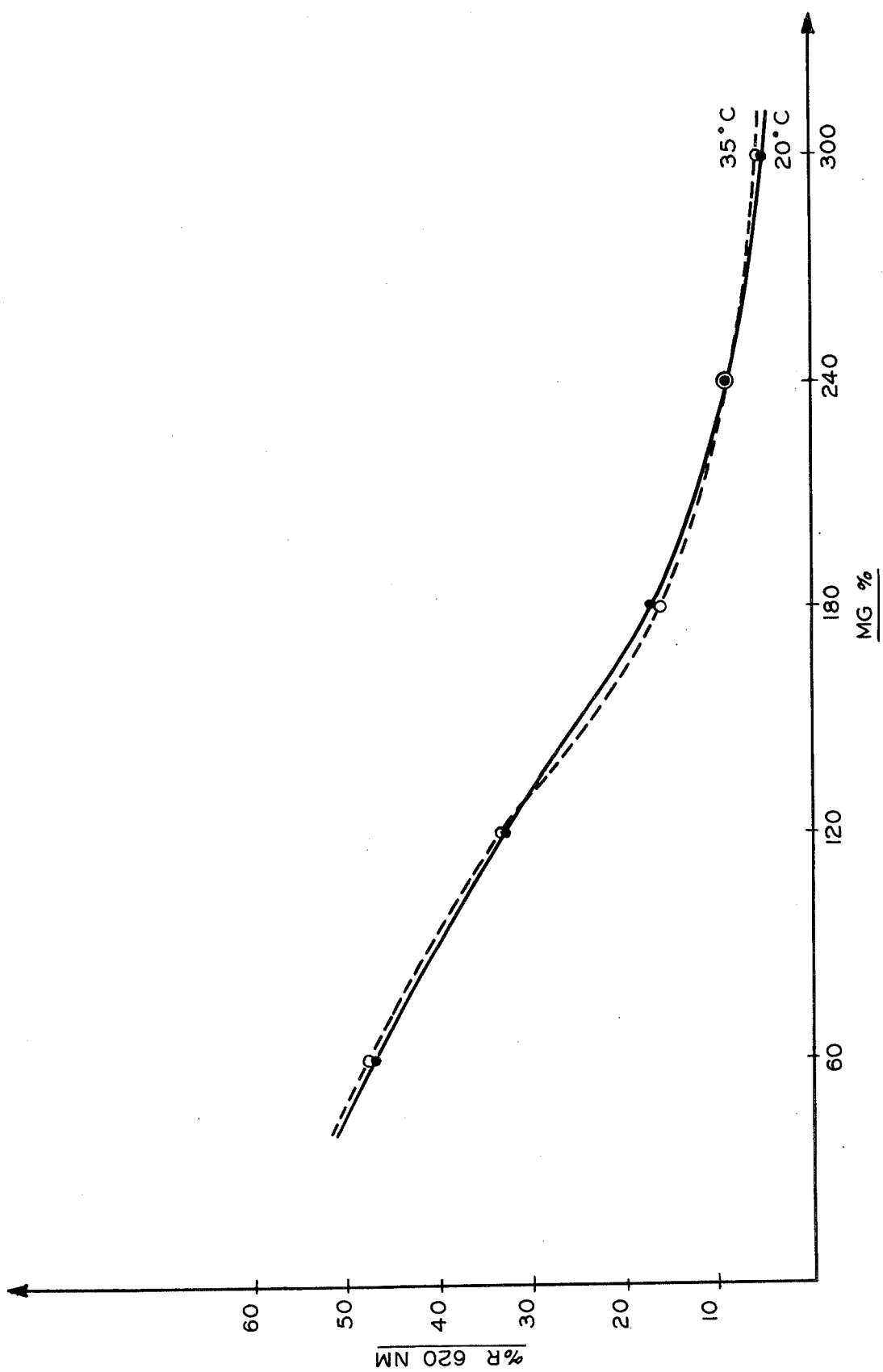

9-SUBSTITUTED 3-AMINOCARBAZOLE COMPOUNDS AND TEST STRIP INDICATOR COMPOSITIONS

This is a division, of application Ser. No. 487,338 filed July 10, 1974.

The present invention is concerned with new 3-aminocarbazole derivatives, with the preparation thereof and with test devices containing the new 3-aminocarbazole derivatives.

U.S. Pat. No. 3,822,285 discloses 9-(γ-aminopropyl)-3-aminocarbazole of the formula:

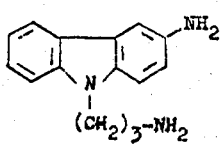

and the salts thereof, processes for the production thereof and of its salts and the use thereof and of its salts as indicators for enzymatic detection reactions, as well as test devices containing this carbazole derivative and/or its salts.

9-(γ-Aminopropyl)-3-aminocarbazole can be used as an indicator for the enzymatic detection of glucose: together with other oxidation indicators, especially with o-tolidine, it gives color values which depend upon the glucose concentration but which are independent of the temperature within wide limits and thus are reproducible. Furthermore, this indicator is not influenced by components which are always commonly in urine, for example acetoacetic acid or ascorbic acid, so that test devices containing the indicator are good diagnostic agents for testing urine.

We have now found that compounds of the following formula are outstandingly suitable for test devices for the determination of glucose:

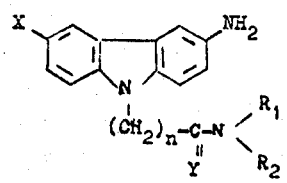

wherein
X is hydrogen or halogen,
Y is oxygen or represents two hydrogen atoms; and
$R_1$ and $R_2$, which can be the same or different, are hydrogen, lower alkyl or hydroxyalkyl or amino; and
n is 1 or 2, with the proviso that when n is 2, X, Y, $R_1$ and $R_2$ cannot all be hydrogen atoms,
as well as the salts thereof with inorganic and organic acids.

The term "lower alkyl" is intended to encompass alkyl of up to 6, preferably up to 4, carbon atoms.

The production of test devices, for example, test papers, test strips and test films, using compounds of formula (I') can be carried out in the manner described in the Main Patent Specificaton, using the formulations given therein.

The new test devices according to the present invention can also be used together with o-tolidine, without the test devices having a greater tendency to be disturbed. Sometimes, this combination results in better color gradations. In the case of the determination of glucose in blood or serum, there are obtained, depending upon the indicator (I') used, yellow to red colorations when the glucose contents are low; in the case of comparatively high glucose contents, the blue to green color of the o-tolidine radical occurs.

Apart from the buffers mentioned in the Main Patent Specification, i.e., phosphate and citrate buffers, there can also be employed less conventional buffers, for example, 3,3-dimethyl-glutarate, mellithate and ethylene-diamine-tetraacetic acid buffers, as well as the so-called Good buffers, insofar as they are effective in a pH range of 4.5 to 7.

The new compounds of formula (I') according to the present invention can be prepared, for example, by one of the following methods;

a. reaction of a compound of the formula:

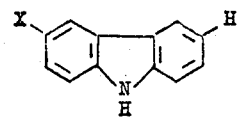

in which X has the same meaning as above, with a compound of the formula:

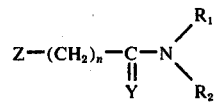

wherein Y, $R_1$, $R_2$ and n have the same meanings as above and Z is a reactive group; or b. reaction of a compound of the formula:

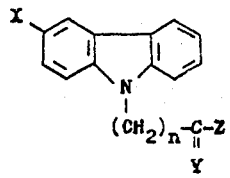

wherein X, Y, Z and n have the same meanings as above, with a compound of the formula:

$R_1 - NH - R_2$     (V)

wherein $R_1$ and $R_2$ have the same meanings as above, whereby, at any desired stage of the reaction, a nitro group is introduced into the 3-position of the carbazole ring which is thereafter reduced to an amino group and whereby, if desired, the compound (I') obtained is reacted with an inorganic or organic acid to give a corresponding salt.

When X is a halogen atom, it can be a fluorine, chlorine, bromine or iodine atom, chlorine being preferred.

The lower alkyl radicals in the above-given formula can contain up to 4 carbon atoms.

The reaction of compounds of formula (II) with compounds of formula (III) can be carried out in an inert solvent, for example toluene, in the presence of a strong base, for example, sodamide.

In the case of the reaction of compounds of formulae (IV) and (V), the latter are preferably used in excess so that the use of a solvent is unnecessary.

The reactive group Z in the compounds of formula (III) can be a halogen atom, preferably a chlorine or bromine atom, or an alkyl sulfonate, tosylate, brosylate or alkoxy radical containing up to 3 carbon atoms.

The nitration, which can be carried out at any desired stage of the reaction, can be carried out with conventional nitration agents and advantageously with glacial acetic acid and nitric acid. The nitro group can be reduced catalytically to an amino group, for example with the use of Raney nickel and hydrogen.

The compounds of formula (I') are generally reacted with acids to give the corresponding simple or double salts. As acids, there can be used, for example, hydrocholoric acid, sulfuric acid, phosphoric acid, hydrobromic acid, boric acid, acetic acid, oxalic acid, lactic acid, citric acid, malic acid, benzoic acid, malonic acid, maleic acid, succinic acid, butyric acid or propionic acid.

The following Examples are given for the purpose of illustrating the preparation of compounds illustrative of the present invention:

EXAMPLE 1

Preparation of 9-(Carbamidomethyl)-3-aminocarbazole 29.83 g. (0.1 mol) 9-(carbethoxymethyl)-3-nitrocarbazole were hydrogenated in 375 ml. 6N methanolic ammonia in the presence of 10 ml. Raney nickel for 4 hours at 50° C. under 10 ats. pressure of hydrogen. After filtering off the catalyst with suction and evaporating the filtrate in a vacuum, there were obtained 27.3 g. of pale brown crystals. After three recrystallizations from isopropanol, there were obtained 8.23 g. (34.3% of theory) pure 9-(carbamidomethyl)-3-aminocarbazole in the form of beige-colored crystals which melted at 220°–222° C. Further quantities of the product could be obtained from the mother liquors. The total yield was then about 50% of theory.

The nitrocarbazole ester used as starting material was prepared in the following manner:

50.6 g. (0.2 mol) 9-(carbethoxymethyl)-carbazole (m.p. 97° C.) were dissolved in 200 ml. glacial acetic acid contained in a 500 ml. three-necked flask equipped with a stirrer, condenser, dropping funnel and thermometer and heated on an oil bath to 80° C. Thereafter, a mixture of 13.2 ml. 65% nitric acid (about 0.2 mol) and 40 ml. glacial acetic acid was added dropwise at 80° C., while stirring, into the acetic acid solution of the ester and the reaction mixture then stirred for a further 30 minutes. After cooling the reaction mixture to ambient temperature, it was poured into 1 liter of water and the crystals formed were filtered off with suction, well washed with water and the dark green crude product recrystallized from acetone. There were obtained 25.8 g. (41.1% of theory) 9-(carbethoxymethyl)-3-nitrocarbazole in the form of yellow crystals which melted at 163° C. Further quantities of the product could be isolated from the mother liquor.

EXAMPLE 2

Preparation of 9-(β-Dimethylaminoethyl)-3-aminocarbazole 25 g. (0.0725 mol) 9-(β-dimethylaminoethyl)-3-nitrocarbazole were hydrogenated in 200 ml. 4.2N methanolic ammonia in the presence of about 17 g. Raney nickel for 3 hours and 16 minutes at 23° – 25° C., using a 1 liter shaking apparatus. The catalyst was then filtered off with suction and washed with methanol. The washings were combined with the filtrate which was evaporated to give 12.75 g. of an oily product. This was dissolved in isopropanol and mixed dropwise, while cooling with ice, with an ethereal solution of hydrogen chloride. The dihydrochloride thus formed was filtered off with suction and dried at 60° C. in a drying cabinet. 16.25 g. 9-(β-dimethylaminoethyl)-3-aminocarbazole dihydrochloride were obtained. After recrystallization from ethanol, 12.4 g. (50.8% of theory) of the desired product were obtained in the form of colorless crystals which melted, with decomposition, at 248° C.

The nitrocarbazole ester used as starting material was prepared in the following manner:

23.7 g. (0.1 mol) 9-(β-dimethylaminoethyl)-carbazole (prepared in the manner described by O. Eisleb, Ber. dtsch. chem. Ges., 74, 1433/1941) in 100 ml. glacial acetic acid were placed in a 500 ml. three-necked flask equipped with a stirrer, thermometer and dropping funnel and placed in an ice-bath. A solution of 8.28 ml. (0.2 mol) anhydrous nitric acid in 50 ml. glacial acetic acid was added dropwise thereto at 15° – 20° C. The reaction mixture was further stirred for an hour at 20° – 25° C. and then poured into 500 ml. ice-water. The precipitated green crystals were filtered off with suction, well washed with water and dried at 80° C. in a drying cabinet. There were obtained 32.4 g. (94% of theory) 9-(β-dimethylaminoethyl)-3-nitrocarbazole which melted, with decomposition, at 190° C.

EXAMPLE 3

Preparation of 9-(β-Dimethylaminoethyl)-6-chloro-3-aminocarbazole 38 g. (0.1 mol) 9-(β-dimethylaminoethyl)-6-chloro-3-nitrocarbazole were hydrogenated at atmospheric pressure in 1 liter methanol in the presence of 30 ml. Raney nickel for a period of 3 hours at 18° – 23° C. After the take up of the calculated amount of hydrogen, the hydrogenation was broken off and the reaction mixture was worked up. The crude product obtained was dissolved in 200 ml. methanol and mixed, while cooling, with 150 ml. 6N ethereal hydrogen chloride solution. The dihydrochloride was thereby formed and the precipitation thereof was completed by the addition of ether. The salt was dissolved in water, treated three times, while warming, with active charcoal and the clarified solution filtered off with suction. After evaporation of the aqueous filtrate, the residue obtained was dissolved in methanol and the dihydrochloride caused to crystallize by the addition of ether. After filtering off with suction and drying, there were obtained 30.1 g. (80.1% of theory) 9-(β-dimethylaminoethyl)-6-chloro-3-aminocarbazole dihydrochloride, which melted, with decomposition, at 280° C.

The nitro compound used as starting material was prepared in the following manner:

10 g. (0.24 mol) sodamide were suspended in 100 ml. dry toluene in a 500 ml. three-necked flask equipped with stirrer, condenser, thermometer, Claisen attachment, dropping funnel and a calcium chloride drying tube, heated to 90° C. and 48 g. (0.24 mol) 3-chlorocarbazole (obtained by the reaction of 1 mol carbazole with 1.3 mol sulfuryl chloride in chloroform; yield 40% of theory) added thereto and, within the course of 30 minutes, 26.8 g. (0.25 mol) β-dimethylaminoethyl chloride added dropwise while stirring, whereafter the reaction mixture was boiled under reflux for 5 hours. After cooling, 30 ml. water were carefully added dropwise and the toluene layer was separated off, dried over anhydrous sodium sulfate and evaporated. 65 g. of a brown oil were obtained. After distillation thereof in a vacuum, there were obtained 59.6 g. (91.5% of theory) 9-(β-dimethylaminoethyl)-6-chlorocarbazole in the form of a yellow oil; b.p. 198° – 201° C./2 mm.Hg.

54.4 g. (0.2 mol) of the carbazole compound thus obtained were dissolved in 250 ml. glacial acetic acid and a solution of 16.6 ml. (0.4 mol) nitric acid (d = 1.51) in 100 ml. glacial acetic acid were added thereto dropwise, while cooling, within the course of 50 minutes. After stirring for 1 hour at 0° C., the nitro compound formed was filtered off with suction, washed twice with 50 ml. amounts of ether and the crude product recrystallized either from a mixture of methanol and water (2:1) or from a mixture of acetone and water (1:0.7). There were obtained 40.3 g. (53.1% of theory) 9-(β-dimethylaminoethyl)-6-chloro-3-nitrocarbazole in the form of yellow crystals which melted, with decomposition, at 217° C. Further products could be obtained from the mother liquor.

EXAMPLE 4

Preparation of
9-(β-Carbohydrazidoethyl)-3-aminocarbazole 2.68 g. (0.01 mol) 9-(β-carbomethoxyethyl)-3-aminocarbazole were placed in a 100 ml. round-bottomed flask equipped with a cooler and a heating bath and then boiled under reflux for 2.5 hours with 50 ml. hydrazine hydrate. Thereafter, excess hydrazine hydrate was distilled off and the residue was recrystallized from isopropanol. There were obtained 2 g. (74.5% of theory) 9-(β-carbohydrazidoethyl)-3-aminocarbazole, which melted at 172° – 174° C.

The 3-aminocarbazole derivative used as starting material was prepared as follows:

100 g. (0.46 mol) 9-(β-cyanoethyl)-carbazole were suspended in 1 liter methanol in a 1 liter three-necked flask equipped with a stirrer, condenser, thermometer and gas inlet tube and dry hydrogen chloride passed therein for 12 hours. The nitrile thereby went completely into solution and ammonium chloride precipitated out. This was filtered off with suction and the filtrate was mixed with 500 ml. water. The precipitated crystals were filtered off with suction and washed with water until free of chloride. There were obtained 105.7 g. (92.4% of theory) 9-(β-carbomethoxyethyl)-carbazole in the form of colorless crystals which melted at 64° – 66° C.

68.25 g. (0.27 mol) of this methyl ester were dissolved in 360 ml. glacial acetic acid in a 1 liter three-necked flask equipped with a condenser, stirrer, thermometer and dropping funnel, whereafter a solution of 22.5 ml. 63% nitric acid in 45 ml. glacial acetic acid was added dropwise, within the course of 30 minutes, at such a rate that a temperature of 30° C. was not exceeded. The reaction mixture was then further stirred for 30 minutes at 20° C. and subsequently poured into 2 liters of water. The green crystals thus obtained were filtered off with suction, washed with water and then with ether. There were obtained 71.65 g. (89.2% of theory) 9-(β-carbomethoxyethyl)-3-nitrocarbazole in the form of pale green crystals with a melting point of 125° – 126° C.

52 g. (0.174 mol) of the nitro ester thus obtained were then hydrogenated in a 2 liter stirrer apparatus in 500 ml. absolute methanol, 1 liter 4N methanolic ammonia and 30 ml. Raney nickel for 4 hours and 20 minutes at 25° C. After filtering off the catalyst with suction, evaporating the residue and drying, there were obtained 45 g. of the corresponding amino ester. The crude product was recrystallized from isopropanol. There were thus obtained 38.6 g. (82.6% of theory) crystalline 9-(β-carbomethoxyethyl)-3-aminocarbazole, which had a melting point of 132° – 134° C.

EXAMPLE 5

Preparation of
9-(β-Hydroxyethylaminocarbonylethyl)-3-aminocarbazole 2.68 g. (0.01 mol) 9-(β-carbomethoxyethyl)-3-amino-carbazole (prepared in the manner described in Example 4) were placed in a 50 ml. round-bottomed flask equipped with a condenser and heating bath and heated under reflux with 20 ml. ethanolamine. Thereafter, excess ethanolamine was distilled off under water-pump vacuum and the residue obtained dissolved in methanol. After the addition of methanolic hydrogen chloride, the crystals formed were filtered off with suction and washed with ether. There were obtained 2.44 g. (73.2% of theory) 9-(β-hydroxyethylaminocarbonylethyl)-3-aminocarbazole hydrochlroide, which had a melting point of 217° – 218° C.

EXAMPLE 6

Preparation of
9-(γ-Dimethyaminopropyl)-3-aminocarbazole 9-(γ-Dimethylaminopropyl)-carbazole was obtained from carbazole and γ-dimethylaminopropyl chloride in a manner analogous to that described in Example 3. The yield was 70.5% of theory, the product being a yellowish oil boiling at 200° – 210° C./1.1 mm.Hg.

Nitration of this compound gave a yield of 62.5% of an ochre-colored 9-(γ-dimethylaminopropyl)-3-nitrocarbazole, which melted at 196° – 207° C. This intermediate was then hydrogenated in the presence of Raney nickel and of methanolic ammonia at 25° – 30° C. and the free base thus obtained was converted into the dihydrochloride. There was obtained a yield of 76.4% of theory of 9-(γ-dimethylaminopropyl)-3-aminocarbazole in the form of colorless crystals which melted, with decomposition, at 245° C.

EXAMPLE 7

Preparation of
9-(γ-Dimethylaminopropyl)-6-chloro-3-aminocarbazole 9-(γ-Dimethylaminopropyl)-3-chlorocarbazole was obtained from 3-chlorocarbazole and γ-dimethylaminopropyl chloride in a manner analogous to that described in Example 3. The yield was 74.2% of theory, the product being a yellowish oil boiling at 240° – 245° C./5 mm. Hg.

Nitration of this compound gave, in a yield of 67.3% of theory, yellow 9-(γ-dimethylaminopropyl)-3-chloro-6-nitrocarbazole, which had a melting point of 219° C. Hydrogenation thereof in the presence of Raney nickel in methanol and conversion of the base thus obtained into the dihydrochloride gave a yield of 73.6% of theory of 9-(γ-dimethylaminopropyl)-6-chloro-3- aminocarbazole dihydrochloride in the form of yellowish crystals which melted, with decomposition, at 276° C.

EXAMPLE 8

Test paper for the detection of glucose in urine

Filter paper was impregnated with a solution of the following composition and dried at 50° C.:

| | |
|---|---|
| 1.2M citrate buffer, pH 5 | 50.0 ml. |
| 9-($\gamma$-dimethylaminopropyl)-6-chloro-3-aminocarbazole dihydrochloride | 0.75 g. |
| glucose oxidase (104 U/mg.) | 0.25 g. |
| peroxidase (63 U/mg.) | 0.05 g. |
| water ad | 100.0 ml. |

The test paper reacted with glucose-containing urine with red-orange to blackish-red color shades. Urine samples of various origins, as well as acetoacetic acid-containing urine samples, all with the same glucose concentration, showed no significant difference in the color shade obtained.

EXAMPLE 9

When, in the formulation given in Example 8, there were used as indicators 0.02 mol amounts of the following indicators, then test papers were obtained with practically the same properties but merely with different reaction colors: 9-($\beta$-dimethylaminoethyl)-6-chloro-3-aminocarbazole dihydrochloride (color gradations from ochre via sepia to black); 9-($\beta$-dimethylaminoethyl)-3-aminocarbazole dihydrochloride (color gradations from yellow via sepia to black).

EXAMPLE 10

Filter paper was impregnated with a solution of the following composition and dried at 50° C.:

| | |
|---|---|
| 1M citrate buffer, pH 6 | 50.0 ml. |
| 9-($\beta$-dimethylaminoethyl)-3-aminocarbazole dihydrochloride | 1.0 g. |
| o-tolidine | 0.4 g. |
| glucose oxidase (104 U/mg.) | 0.3 g. |
| peroxidase (63 u/mg.) | 0.06 g. |
| sodium lauryl sulfate | 0.1 g. |
| ethanol | 33.0 ml. |
| water ad | 100.0 ml. |

The test paper gave, with glucose-containing urine samples, color gradations from yellow via brown-olive to green. Urine samples of different origins, as well as acetoacetic acid-containing urine samples, all with the same glucose concentration, showed no significant differences in color.

EXAMPLE 11

Test film for the detection of glucose in blood

| | | |
|---|---|---|
| Components: | | |
| polyvinyl acetate propionate dispersion | | 45.0 g. |
| 1.85% solution of sodium alginate in 0.5M phosphate buffer, pH 5.5 | | 35.0 g. |
| sodium nonyl sulfate dissolved in 5.0 ml. water | | 0.75 g. |
| glucose oxidase (62.7 U/mg.) | dissolved, in 10 ml | 0.189 g. |
| peroxidase (68.8 U/mg.) | water | 0.235 g. |
| o-tolidine dissolved in 2.5 ml. acetone | | 0.600 g. |
| 9-($\beta$-hydroxyethyl)-aminocarbonylethyl]-3-aminocarbazole hydrochloride dissolved in 2.0 ml. water | | 0.035 g. |

The components were well mixed, applied with a layer thickness of 300 $\mu$ to a film of polyvinyl chloride and dried for 35 minutes at 60° C. Upon dropping glucose-containing blood thereon, then wiping off the blood after one minute and leaving for a further 2 minutes, there were obtained the following reaction colors which are independent of the temperature:

| | |
|---|---|
| 60 mg. % glucose | - brownish red |
| 120 mg. % glucose | - brown-red |
| 180 mg. % glucose | - dark olive |
| 240 mg. % glucose and more | - green of increasing color depth. |

FIG. 1 of the accompanying drawing shows the calibration curves measured at 20° C. and 35° C. with a conventional remission photometer.

EXAMPLE 12

Test films according to Example 11 which, instead of 0.035 g. 9-[($\beta$-hydroxyethyl)-aminocarbonylethyl]-3-aminocarbazole hydrochloride, contained 0.025 g. 9-($\beta$-carbamidoethyl)-3-aminocarbazole (A) or 0.034 g. 9-($\beta$-dimethylaminoethyl)-3-aminocarbazole dihydrochloride (B), reacted with glucose-containing blood in a temperature-independent reaction with the following color:

TABLE

| mg. % glucose | A | B |
|---|---|---|
| 60 | brownish-red | beige |
| 120 | olive | greenish-beige |
| 180 | brownish-green | yellowish-green |
| 240 and more | green with increasing color depth | green with increasing color depth |

It will be understood that the foregoing specification and examples are illustrative but not limitative of the present invention inasmuch as other embodiments within the spirit and scope of the invention will suggest themselves to those skilled in the art.

We claim:

1. Diagnostic test composition for enzymatic determination of glucose containing a 9-substituted 3-aminocarbazole compound of the formula:

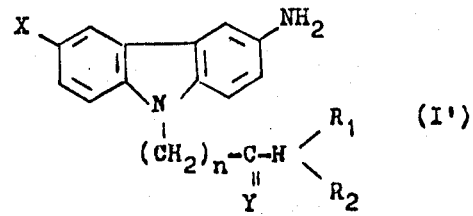

wherein
X is hydrogen or halogen,
Y is oxygen or represents two hydrogen atoms; and
$R_1$ and $R_2$, which can be the same or different, are hydrogen, lower alkyl or hydroxyalkyl or amino; and n is 1 or 2, with the proviso that when n is 2, X, Y, $R_1$ and $R_2$ cannot be hydrogen atoms, as well as the salts thereof with inorganic and organic acids, and glucose oxidase and peroxidase.

2. Test composition as claimed in claim 1 wherein said glucose indicator chromogen is o-tolidine.

3. Test composition as claimed in claim 1 in the form of a test film having the reagents incorporated thereinto.

4. Test composition as claimed in claim 1 in the form of a test strip comprising an absorbent carrier.

5. Test composition as claimed in claim 1 wherein X in the formula is hydrogen.

6. Test composition as claimed in claim 1 wherein X in the formula is halogen.

7. Test composition as claimed in claim 1 wherein Y in the formula is oxygen.

8. Test composition as claimed in claim 1 wherein Y in the formula represents two hydrogen atoms.

9. Test composition as claimed in claim 1 wherein at least one of $R_1$ and $R_2$ in the formula is lower alkyl.

10. Test composition as claimed in claim 1 wherein at least one of $R_1$ and $R_2$ in the formula is hydroxyalkyl.

11. Test composition as claimed in claim 1 wherein at least one of $R_1$ and $R_2$ in the formula is amino.

12. Test composition as claimed in claim 1 wherein n in the formula is 2 and at least one of X, Y, $R_1$ and $R_2$ in the formula is other than hydrogen.

13. Test composition as claimed in claim 1 wherein X in the formula is halogen and Y in the formula represents two hydrogen atoms.

14. Test composition as claimed in claim 1 wherein X in the formula is hydrogen and n in the formula is 1.

15. Test composition as claimed in claim 1 which additionally comprises a known glucose indicator chromogen.

* * * * *